(12) United States Patent
Zeile et al.

(10) Patent No.: US 8,502,142 B2
(45) Date of Patent: Aug. 6, 2013

(54) CHARGED PARTICLE BEAM ANALYSIS WHILE PART OF A SAMPLE TO BE ANALYZED REMAINS IN A GENERATED OPENING OF THE SAMPLE

(75) Inventors: Ulrike Zeile, Heidenheim (DE); Dietmar Donitz, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 12/584,992

(22) Filed: Sep. 15, 2009

(65) Prior Publication Data
US 2010/0133432 A1 Jun. 3, 2010

(30) Foreign Application Priority Data
Sep. 17, 2008 (DE) .......................... 10 2008 042 179

(51) Int. Cl.
*G21K 5/10* (2006.01)
*G01F 23/00* (2006.01)
(52) U.S. Cl.
USPC .. 250/306; 250/307; 250/440.11; 250/442.11
(58) Field of Classification Search
USPC .................. 250/306, 307, 440.11, 442.11
See application file for complete search history.

(56) References Cited

U.S. PATENT DOCUMENTS

| 5,270,552 | A | 12/1993 | Ohnishi et al. |
| 6,188,068 | B1 | 2/2001 | Shaapur et al. |
| 6,414,307 | B1 * | 7/2002 | Gerlach et al. ............... 250/307 |
| 6,570,170 | B2 | 5/2003 | Moore |
| 6,664,552 | B2 | 12/2003 | Shichi et al. |
| 6,670,610 | B2 * | 12/2003 | Shemesh et al. .................. 850/9 |
| 6,963,068 | B2 | 11/2005 | Asselbergs et al. |
| 7,067,823 | B2 * | 6/2006 | Iwasaki et al. ........... 250/442.11 |
| 7,297,965 | B2 * | 11/2007 | Kidron et al. .............. 250/492.2 |
| 7,408,178 | B2 | 8/2008 | Tappel |
| 7,423,263 | B2 * | 9/2008 | Hong et al. ............. 250/442.11 |
| 7,888,639 | B2 * | 2/2011 | Tokuda et al. ................ 250/310 |
| 2003/0127595 | A1 * | 7/2003 | Nakamura et al. ........... 250/311 |
| 2003/0183776 | A1 * | 10/2003 | Tomimatsu et al. .......... 250/304 |
| 2004/0089821 | A1 * | 5/2004 | Shichi et al. ............. 250/442.11 |
| 2004/0135096 | A1 * | 7/2004 | Fukuda et al. ........... 250/442.11 |
| 2004/0227082 | A1 * | 11/2004 | Adachi et al. ................ 250/311 |
| 2006/0011867 | A1 * | 1/2006 | Kidron et al. ............ 250/492.21 |
| 2006/0113496 | A1 * | 6/2006 | Yoshioka .................. 250/492.21 |
| 2006/0157341 | A1 * | 7/2006 | Fujii ........................ 204/192.34 |

(Continued)

FOREIGN PATENT DOCUMENTS
DE 10 2007 026 847 A1 12/2008

OTHER PUBLICATIONS

Imaging and analysis of subsurface Cu interconnects by detecting backscattered electrons in the scanning electron microscope L. M. Gignac, M. Kawasaki, S. H. Boettcher, and O. C. Wells Citation: J. Appl. Phys. 97, 114506 (2005); doi: 10.1063/1.1927276.*

*Primary Examiner* — Phillip A Johnston
*Assistant Examiner* — Brooke Purinton
(74) *Attorney, Agent, or Firm* — Muirhead and Saturnelli, LLC (57) ABSTRACT

A device and method for analyzing a sample provide for extracting a part to be analyzed from the sample with the aid of a previously generated opening in the sample. The part to be analyzed is examined in greater detail with the aid of a particle beam. For this purpose, the sample is placed in the opening or on a sample holder.

23 Claims, 9 Drawing Sheets

U.S. PATENT DOCUMENTS

| | | |
|---|---|---|
| 2008/0067385 A1* | 3/2008 | Tokuda et al. .............. 250/310 |
| 2008/0135779 A1* | 6/2008 | Shichi et al. ............. 250/440.11 |
| 2008/0258056 A1* | 10/2008 | Zaykova-Feldman et al. .......................... 250/307 |
| 2009/0078867 A1* | 3/2009 | Avinun-Kalish et al. ..... 250/309 |
| 2009/0218488 A1* | 9/2009 | Wells .......................... 250/307 |
| 2009/0230299 A1* | 9/2009 | Shichi et al. ................ 250/282 |
| 2010/0025580 A1* | 2/2010 | Hammer et al. ......... 250/442.11 |
| 2010/0133432 A1* | 6/2010 | Zeile et al. .................... 250/307 |

* cited by examiner

CHARGED PARTICLE BEAM ANALYSIS WHILE PART OF A SAMPLE TO BE ANALYZED REMAINS IN A GENERATED OPENING OF THE SAMPLE

TECHNICAL FIELD

This application relates to a device and method for analyzing a sample and, in particular, analyzing a sample using a particle beam device.

BACKGROUND OF THE INVENTION

In the field of material analysis, for example, in the field of semiconductor technology, cross sections of a sample are generated and examined in detail.

For this purpose, a method is known from the prior art in which a sample is initially prepared and subsequently examined in a particle beam device. The sample is prepared in a first particle beam device, which has both an electron beam column and an ion beam column. With the aid of an electron beam, which is provided by the electron beam column, a part of the sample to be analyzed is initially identified. This part of the sample to be analyzed is then prepared with the aid of an ion beam which is provided by the ion beam column and cut out of the sample. The part of the sample that has been cut out and is to be analyzed is subsequently taken out of the first particle beam device and then taken into a second particle beam device in the form of a transmission electron microscope. Further examinations are then performed on the part of the sample to be analyzed with the aid of the second particle beam device.

It is, however, disadvantageous in this known method that the part of the sample to be analyzed must be taken out of the first particle beam device and taken into the second particle beam device. It may well happen then that the part of the sample to be analyzed is contaminated in such a way that further examination with the aid of the second particle beam device (transmission electron microscope) can no longer be performed. In addition, the method is very time-consuming due to the taking-out operation. Furthermore, taking out always carries the risk that the part of the sample to be analyzed becomes damaged, so that it may not be further examined.

It is conceivable to examine the part of the sample to be analyzed also in the first particle beam device, so that the part of the sample to be analyzed does not have to be taken out of the first particle beam device. However, only an examination that does not provide sufficient spatial resolution is then possible. For reasons of geometry, the part of the sample to be analyzed may be examined in the first particle beam device only from an oblique angle. Therefore, a particle beam is basically directed to the part of the sample to be analyzed at an oblique angle. This impairs the spatial resolution. In addition, an image of the part of the sample to be analyzed may be distorted.

Another method for analyzing a sample is known from the prior art, which is carried out in a vacuum chamber of a single particle beam device and in which taking out a sample and putting it in again are not necessary. In this known method, a part of a sample to be analyzed is cut out from the sample with the aid of an ion beam. After being cut out, the part to be analyzed is fastened in a holder and lifted out of the sample. The lifted out part of the sample to be analyzed is fastened to an object holder to then be examined with the aid of an electron beam. Electrons transmitted through the part of the sample to be analyzed are detected during the examination. The detected transmitted electrons are used for drawing conclusions about the material of the part of the sample to be analyzed.

Reference is made to U.S. Pat. No. 6,963,068 B2, which is incorporated herein by reference, regarding the above prior art.

The above-described known methods share the common feature that the sample is analyzed in transmission. Therefore, generating the sample or the part of the sample to be analyzed is very complicated because the sample must be generated in the form of a thin sample slice having a thickness of only a few nm, which, however, must still contain the relevant part of the sample.

Accordingly, it would be desirable to provide a device and method which makes it possible to generate the part of the sample to be analyzed and to analyze it in a simpler manner.

SUMMARY OF THE INVENTION

According to the system described herein, a method of analyzing a sample is provided for a sample composed of at least one sample material in which a part of the sample to be analyzed is first identified. Subsequently, an opening may be introduced in the sample material with the aid of a particle beam in such a way that the opening is at least partially adjacent to the part of the sample to be analyzed. Furthermore, the opening may be configured in such a way that at least one surface of the part of the sample to be analyzed may be completely accommodated in the opening. Furthermore, the method according to the system described herein may include separating the part of the sample to be analyzed from the sample material with the aid of the particle beam. The part of the sample to be analyzed may then be examined in greater detail.

In the method according to the system described herein, a part of the sample to be analyzed and removed from the sample may be analyzed by detecting the particles backscattered from the part of the sample to be analyzed or emitted from the part of the sample to be analyzed. Particles emitted from the part of the sample to be analyzed are understood as particles whose kinetic energy at least substantially differs from the kinetic energy of the particles in the particle beam incident on the part of the sample to be analyzed, in particular particles that have a kinetic energy of less than 100 eV. According to the method, it is possible, for analyzing the part of the sample to be analyzed, to detect only particles that exit on the side of the part of the sample to be analyzed which is hit by the particle beam. In this way the part of the sample to be analyzed may have a substantially greater thickness than in methods in which particles transmitted through the sample are detected. This makes generating the part of the sample to be analyzed having the relevant cross-section of the sample less critical and simpler.

Furthermore, in the method according to the system described herein, the part of the sample to be analyzed may be analyzed in the same sample chamber or vacuum chamber in which the part of the sample to be analyzed is cut and thus removed from the sample.

The system described herein therefore has the advantage that the part of the sample to be analyzed, after being separated from the sample material, does not have to be taken out of the particle beam device for further examination. Thus, contamination of the part of the sample to be analyzed prior to being examined is prevented. In contrast with the prior art in which the part of the sample is taken out, as discussed above, the method according to the system described herein is also less time-consuming. In addition, the risk of damaging the part of the sample to be analyzed, which may well happen in a taking-out operation, is reduced. Furthermore, it is advantageous in the method according to the system described herein that particles backscattered and/or emitted from the part of the sample to be analyzed may be detected and used for the analysis. In particular, backscattered electrons and/or emitted electrons (secondary electrons) are detected. In addition, the part of the sample to be analyzed may be irradiated using a particle beam for examining the part to be analyzed in such a way that the particle beam may be directed perpendicularly or at least approximately perpendicularly onto the part of the sample to be analyzed. The part of the sample to be analyzed does not have to be tilted and is not situated at an oblique angle to the incident particle beam. In this way, high spatial resolution is achieved. Furthermore, image distortions, which have been described above, are prevented.

In an embodiment of the method according to the system described herein, the particle beam, which is provided for generating the opening, may be provided as a first particle beam. The part of the sample to be analyzed may then be placed on a sample holder. Subsequently, the part of the sample to be analyzed may be examined with the aid of a second particle beam. For this purpose, the sample holder may be moved, for example, in such a way that the second particle beam hits the part of the sample to be analyzed perpendicularly or at least approximately perpendicularly. In addition, it is provided that, if needed, the part of the sample to be analyzed may be further prepared, for example, with the aid of the first particle beam, prior to being examined. In another embodiment, it is provided that the part of the sample to be analyzed may initially be placed on a manipulation device, using which the part of the sample to be analyzed may be lifted out of the sample material. It may then be placed on the sample holder.

In another embodiment of the method according to the system described herein, it is also provided that the particle beam used for generating the opening may be configured as a first particle beam. In this embodiment, the part of the sample to be analyzed may be placed in the opening in the sample material. Subsequently, the part of the sample to be analyzed may be examined with the aid of a second particle beam. The part of the sample to be analyzed may be placed in the opening in such a way that a surface of the part of the sample to be analyzed which corresponds to a cross-section surface of the sample, i.e., a section surface which is oriented substantially perpendicularly to the sample surface, is oriented in the opening substantially parallel to the surface of the sample. Due to this positioning in the opening, it is achieved that, during analysis of the part of the sample to be analyzed, the particle beam may be directed to the part of the sample to be analyzed in such a way that the particle beam may hit the surface of the part of the sample to be analyzed corresponding to the cross-section surface of the sample perpendicularly or at least approximately perpendicularly.

Furthermore, it is provided in the method according to the system described herein that an ion beam may be used as the first particle beam and/or an electron beam may be used as the second particle beam. In particular, it is provided that the opening may be introduced in the sample material with the aid of the ion beam and the part of the sample to be analyzed may be separated from the sample material with the aid of the ion beam. The part of the sample to be analyzed may then be examined in greater detail with the aid of the electron beam. The secondary particles generated via interaction of the electron beam with the sample material, in particular the electrons backscattered or emitted from the sample material, may be detected.

It should be explicitly pointed out that the first particle beam and the second particle beam do not necessarily have to be different from each other. Instead, various embodiments of the method according to the system described herein are provided in which the first particle beam and the second particle beam are configured identically, for example, as an ion beam. In this embodiment, the opening in the sample material may be generated with the aid of the ion beam and the part of the sample to be analyzed may be separated from the sample material with the aid of the ion beam. By directing the ion beam to the part of the sample to be analyzed, secondary ions are generated, which are then examined by mass spectrometry, for example, to draw conclusions about the material of the sample.

In another embodiment of the method according to the system described herein, the part of the sample to be analyzed may be identified with the aid of the second particle beam. In the case where the second particle beam is configured as an electron beam, images of the sample may be calculated and displayed with the aid of the detected backscattered electrons or the emitted electrons, on the basis of which the identification may be performed.

The part of the sample to be analyzed may be placed in the opening in the sample material, at least in part, by gravity. This embodiment of the method according to the system described herein is based on the consideration that the part of the sample to be analyzed may be separated from the sample material in such a way that the part of the sample to be analyzed drops into the opening generated in the sample material by itself. However, it should be explicitly pointed out that the system described herein is not limited to placing the part of the sample to be analyzed in the opening by gravity. Instead, the part of the sample to be analyzed may be placed in the opening in the sample in any suitable way. For example, in another embodiment of the method according to the system described herein, it is provided that the part of the sample to be analyzed may be pushed into the opening generated in the sample material with the aid of a manipulator device.

In another embodiment of the method according to the system described herein, it is provided that the part of the sample to be analyzed may be separated using the opening. Subsequently the part of the sample to be analyzed may be placed in the opening or dropped into the opening. In addition, it may be provided that the part of the sample to be analyzed may be subsequently placed on the above-mentioned sample holder. As further discussed in more detail elsewhere herein, in an embodiment of the system described herein, it is provided that multiple openings may be introduced in the sample material. For example, it is provided that a first opening and a second opening may be introduced in the sample material. The first opening may receive the part of the sample to be analyzed. The second opening may be smaller than the first opening. In this embodiment, the part of the sample to be analyzed may be separated using the first opening.

Another embodiment provides that both the first opening and the second opening may have substantially identical dimensions. In this embodiment, the part of the sample to be analyzed may be optionally placed in the first opening or in the second opening. In this embodiment, the separation may be performed using the opening in which the part of the sample to be analyzed is to be placed.

In another embodiment of the method according to the system described herein, at least one section surface, which is initially positioned perpendicularly or at least approximately perpendicularly to a surface of the sample, may be generated by separating the part of the sample to be analyzed from the sample material. The section surface may be placed in the opening when positioning the part of the sample to be analyzed in such a way that the section surface is parallel or at least approximately parallel to the surface of the sample. In this way it is then possible to easily examine the section surface with the aid of the particle beam. In particular it is possible to examine the section surface by irradiating it perpendicularly with the aid of the particle beam. When using a first particle beam and a second particle beam, the section surface may be examined with the aid of the second particle beam for example. In another embodiment, it is provided that, prior to placing the part of the sample to be analyzed in the opening, the section surface may be prepared, in particular, polished, with the aid of the particle beam. The section surface may be oriented approximately parallel to the incident particle beam during the preparation. When using a first particle beam and a second particle beam, the first particle beam may be used for the preparation, for example.

In another embodiment of the system described herein, it is provided that at least one section surface may be generated by separating the part of the sample to be analyzed from the sample material. The section surface may then be positioned after placing the part to be analyzed on the sample holder in such a way that the particle beam hits the section surface perpendicularly. When using a first particle beam and a second particle beam, the second particle beam may hit the section surface perpendicularly, for example. Also in this embodiment of the system described herein, it may be provided that the section surface is prepared, in particular, polished, prior to directing the particle beam onto the section surface.

In another embodiment of the system described herein, it is provided that the part of the sample to be analyzed may be separated in such a way that the part of the sample to be analyzed has a first dimension in a first direction, a second dimension in a second direction, and a third dimension in a third direction. The first and second directions may extend parallel to a surface of the sample; the third direction may extend perpendicular to this surface. The first and third dimensions form the length and width of the part of the sample to be analyzed. For example, the second dimension in the second direction may be 1 µm to 20 µm, or, more particularly, 5 µm to 15 µm. The second dimension corresponds to the thickness of the part of the sample to be analyzed. It is designed in such a way that, when irradiated using a particle beam, no interaction particles are transmitted through the sample and the sample is stable in such a way that it does not break easily. Considerations have led to the conclusion that the part of the sample to be analyzed may have a length of approximately 10 µm to approximately 200 µm, a width of approximately 5 µm to approximately 100 µm, and a thickness of approximately 0.5 µm to 20 µm. The system described herein is, however, not limited to the above-mentioned dimensions of the part of the sample to be analyzed. Instead, any dimension that is suitable for carrying out the method according to the system described herein may be used. In an embodiment of the system described herein, it is also provided that the interaction particles transmitted through the sample may also be detected and evaluated.

In another embodiment of the method according to the system described herein, the opening in the sample material may be generated in such a way that the opening has a first opening dimension in the first direction, a second opening dimension in the second direction, and a third opening dimension in the third direction. The first and second directions may again extend parallel to a surface of the sample; the third direction may extend perpendicular to this surface. The first opening dimension may be greater than or equal to the first dimension of the part of the sample to be analyzed. Furthermore, the second opening dimension may be greater than the second dimension of the part of the sample to be analyzed. The third opening dimension may again be greater than or equal to the third dimension of the part of the sample to be analyzed. The above-mentioned opening dimensions may be selected in such a way that the part of the sample to be analyzed may be placed into the opening without difficulty. In particular, the first opening dimension may also be greater than the third dimension of the part of the sample to be analyzed. The part of the sample to be analyzed may then be examined in sufficient detail. In another embodiment, the part of the sample to be analyzed may be fully inserted in the opening in the sample material.

In yet another embodiment of the method according to the system described herein, multiple openings are provided. Thus, the opening already described previously may be configured as a first opening, which may be adjacent to a first side of the part of the sample to be analyzed. In addition, when the part of the sample to be analyzed is separated from the sample material, a second opening may also be generated, the second opening being situated on a second side of the part of the sample to be analyzed which lies opposite to the first side of the part of the sample to be analyzed. It is also provided that, after placing the part of the sample to be analyzed in the opening, the second side of the part of the sample to be analyzed may face the incident particle beam, for example, the second particle beam. Thus, the second side, which will be examined in greater detail with the aid of the particle beam, for example, the second particle beam, may be basically exposed relatively late. The risk of the second side being contaminated is thus reduced. The second side may correspond to the above-mentioned section surface.

According further to the system described herein, a method for analyzing a sample is provided for a sample composed of at least one sample material in which a part of the sample to be analyzed is first identified. Subsequently an opening may be introduced in the sample material with the aid of a particle beam in such a way that the opening is at least partially adjacent to the part of the sample to be analyzed. Furthermore, the method according to the system described herein may include separating the part of the sample to be analyzed from the sample material with the aid of the first particle beam. After the separation, the part of the sample to be analyzed may be placed in the opening in the sample material. Subsequently, the part of the sample to be analyzed may be examined with the aid of a second particle beam. The above-described method is based on the same basic idea as the method already described above. Furthermore, it may be combined with any of the above-mentioned features or feature combinations.

According further to the system described herein, a particle beam device is provided for carrying out a method having one of the above-mentioned features or a combination of the above-mentioned features. The particle beam device may be used with a sample which is composed of at least one sample material. Furthermore, at least one identifying device is provided for identifying a part of the sample to be analyzed. The identifying device may include, for example, an electron beam column which provides an electron beam. By detecting the particles generated by the interaction of the electron beam with the sample material, a surface of the sample may be displayed as an image.

In addition, at least one opening generator may be provided for generating an opening in the sample material with the aid of a first particle beam that is provided with the particle beam device, the opening being at least partially adjacent to the part of the sample to be analyzed. Furthermore, at least one separating device may be provided for separating the part of the sample to be analyzed from the sample material with the aid of the first particle beam. Furthermore, at least one examining device may be provided for examining the part of the sample to be analyzed with the aid of a second particle beam.

According further to the system described herein, a method for analyzing a sample having a sample surface includes identifying a part of the sample to be analyzed, including finding a particularly relevant location on the sample surface. Furthermore, a first separating surface may be generated between the part of the sample to be analyzed and the sample at a distance from the particularly relevant location, the first separating surface being inclined to the sample surface at an angle different from 0° and 180°. Furthermore, a second separating surface may be generated between the part of the sample to be analyzed and the sample, the second separating surface being inclined to the sample surface at an angle different from 0° and 180° and the second separating surface containing the particularly relevant location. The method may also include the step of polishing only the second separating surface with the aid of a particle beam and the step of separating the part of the sample to be analyzed from the sample by generating further separating surfaces. It is also provided in the method that the second separating surface may be oriented perpendicularly or at least approximately perpendicularly to the optical axis of a particle beam device. Furthermore, in the method, the second separating surface may be analyzed by detecting particles leaving the part to be analyzed on the side of the second separating surface. At least the polishing step of the second separating surface and the step of analyzing the second separating surface may be performed in the same vacuum chamber without the part to be analyzed being taken out of the vacuum chamber between the two steps.

In an embodiment of the above-noted method, it is provided that the second separating surface may be scanned using a focused particle beam for its analysis. In a further embodiment of the method, an electron beam or an ion beam may be used as the focused particle beam. The focused particle beam may provide a spatial resolution perpendicularly to its beam direction of less than 5 nm, in particular of less than 1 nm.

Commercially available scanning electron microscopes make electron probes possible whose diameters are so small that the achievable resolutions perpendicularly to the direction of incidence of an electron beam are less than 5 nm, sometimes even less than 1 nm, in particular when the surface of the sample to be analyzed is oriented perpendicularly to the optical axis of the device and may be positioned at a sufficiently small working distance of a few (1 to 5) mm from the objective of the scanning electron microscope. The above-described methods according to the system described herein may therefore be carried out without difficulties using regular scanning electron microscopes.

BRIEF DESCRIPTION OF THE DRAWINGS

Embodiments of the system described herein are explained in more detail below with reference to the figures, which are briefly described as follows.

DETAILED DESCRIPTION OF VARIOUS EMBODIMENTS

Figure 1:
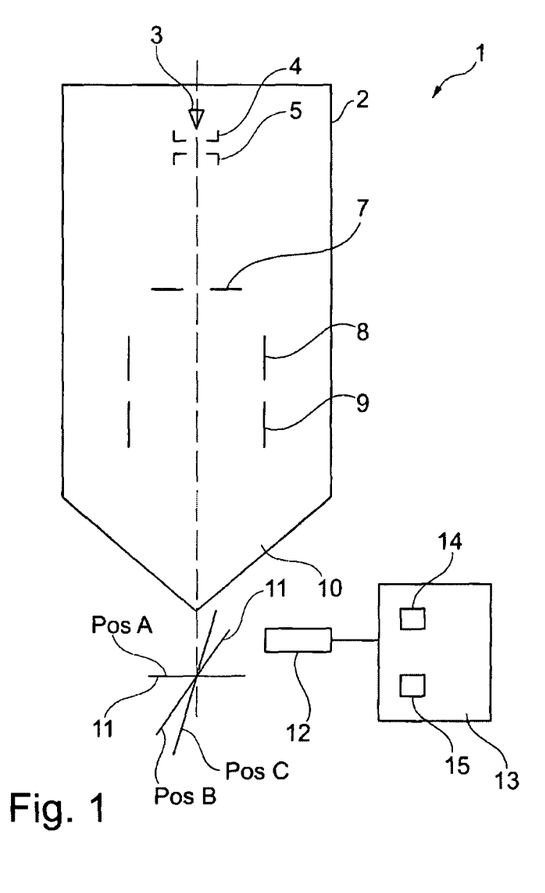
FIG. 1 shows a schematic representation of a particle beam device for analyzing a sample according to an embodiment of the system described herein.
Figure 1A:
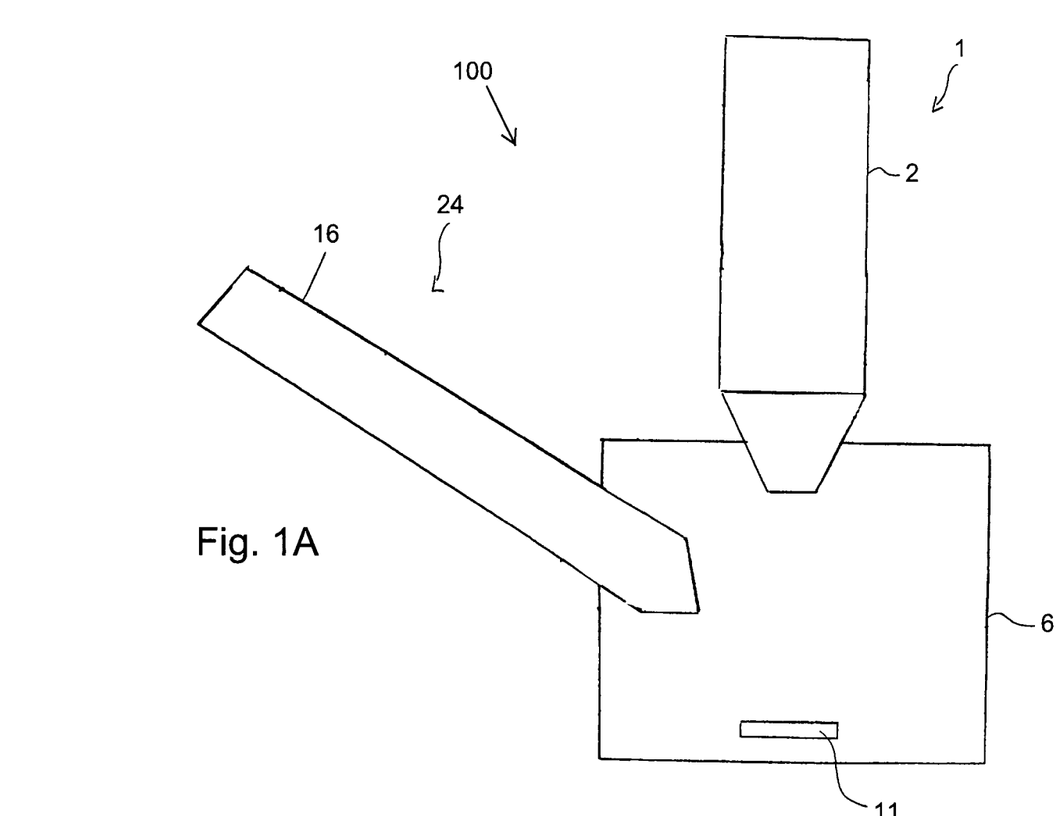
FIG. 1A shows another schematic representation of the particle beam device of FIG. 1.

FIGS. 1 and 1A show a schematic representation of a particle beam device 100 which has an ion beam device 1 and an electron beam device 24, which are arranged at a sample chamber 6 (vacuum chamber) according to an embodiment of the system described herein. Methods for analyzing a sample, as further discussed elsewhere herein, may be carried out using the illustrated particle beam device 100.

The ion beam device 1 may have an ion beam column 2 in which numerous units of the ion beam device 1 are situated. In particular, an ion source 3 may be situated in the ion beam column 2. The ion source 3 may generate ions which form an ion beam in the ion beam column 2. The ions may be accelerated to a predefinable potential with the aid of an electrode 4 and then passed through a condenser lens 5. The ion beam formed by the ions may be passed through an aperture 7 and then reach a first deflecting system 8 and a second deflecting system 9, which may comprise a scanning device. The ion beam formed by the ions may be scanned over a sample 11, which is situated in the sample chamber 6, with the aid of the first deflecting system 8 and the second deflecting system 9. Beforehand, the ion beam may be focused onto the sample 11 with the aid of an objective lens 10.

The electron beam device 24 may include a scanning electron microscope. It has an electron column 16, in which the units of the electron beam device 24 are situated. Thus, an electron source 17 may be provided, which generates electrons which are extracted with the aid of a first electrode 18. The electrons may be accelerated to a predefinable potential with the aid of a second electrode 19. The electrons may then be passed through a condenser lens 20, whereby an electron beam is formed, which, with the aid of an objective lens 21, is focused onto the sample 11. Scanning electrodes (not illustrated) may be arranged at the objective lens 21 and ensure that the electron beam may be scanned over the sample 11.

When the electron beam hits the sample 11, interaction particles are generated, in particular secondary electrons and electrons scattered back (also referred to herein as backscattered electrons), which may be detected with the aid of a first detector 22 and a second detector 23 and used for imaging. It is thus possible to image the surface of the sample 11.

Figure 2:
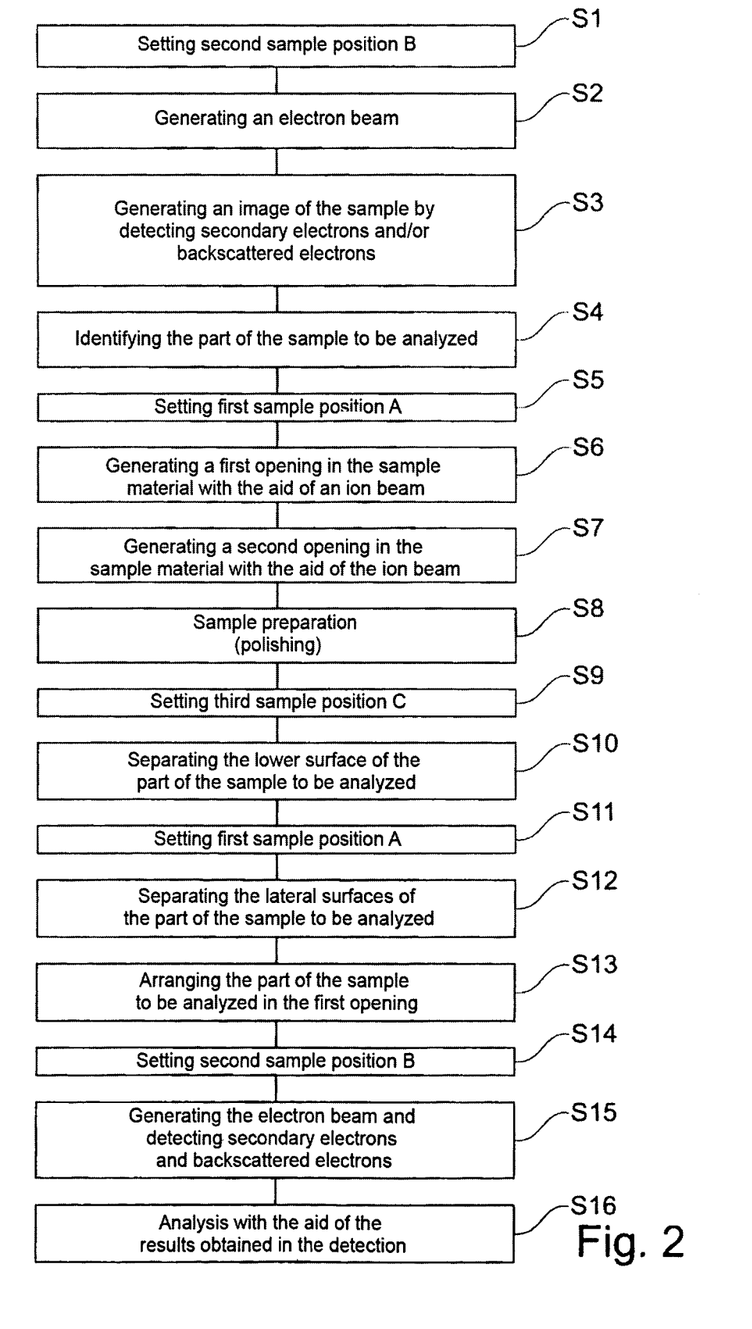
FIG. 2 shows a flow chart of a method for analyzing a sample according to an embodiment of the system described herein.

FIG. 2 schematically shows the sequence of an embodiment of the method according to the system described herein, which may be carried out with the aid of the above-mentioned particle beam device 100. Initially, in a first method step S1, the sample 11 may be brought into a second sample position B. In this second sample position B, an electron beam may be generated in method step S2 that hits the surface of the sample 11 perpendicularly. This makes it possible to image the surface of the sample 11 by detecting secondary electrons and/or backscattered electrons, which are generated due to the interaction of the sample material with the incident electron beam (method step S3).

Figure 3:
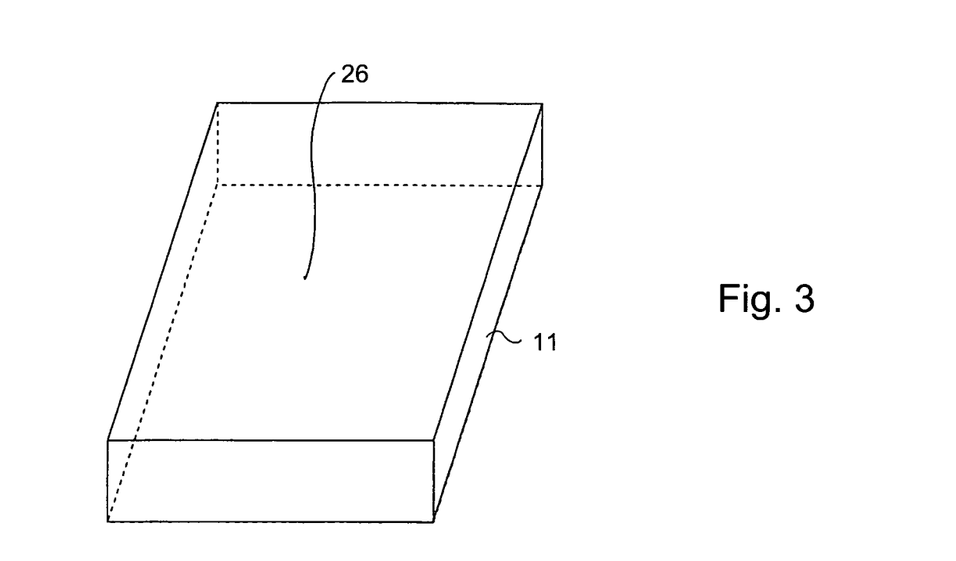
FIG. 3 shows a schematic representation of a sample according to an embodiment of the system described herein.

In a further method step S4, a part 26 of the sample 11 to be analyzed may be identified on the basis of the image. In particular, a particularly relevant location in the part 26 of the sample 11 to be analyzed may be identified. The sample 11 is schematically shown again in FIG. 3.

Figure 4:
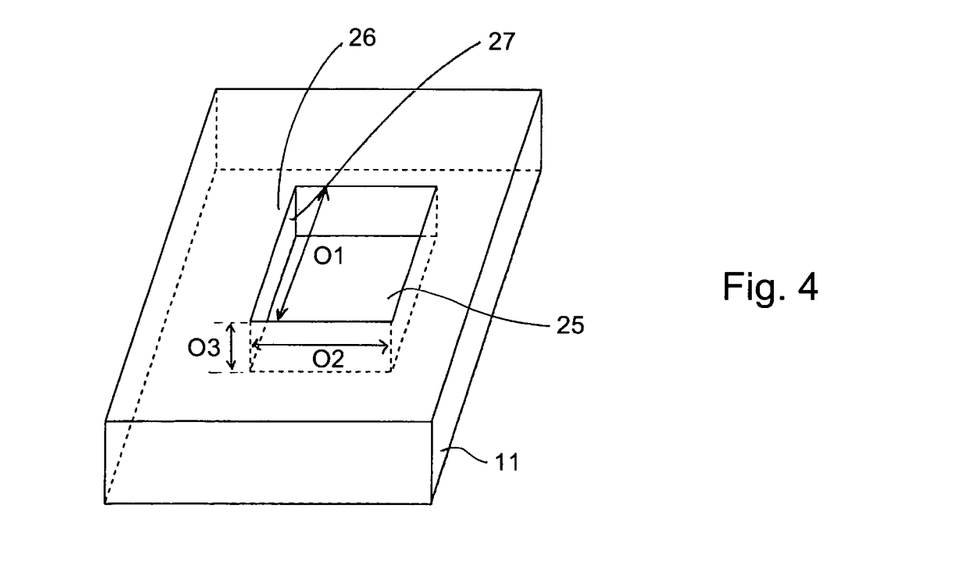
FIG. 4 shows another schematic representation of the sample of FIG. 3, the sample having an opening.

The sample 11 may then be brought into a first sample position A (method step S5). In the first sample position A, an ion beam generated by the ion beam device 1 hits the sample 11 perpendicularly. Subsequently, in a method step S6, a first opening 25 may be introduced in the material of the sample 11 with the aid of the ion beam (see also FIG. 4). For this purpose, the ion beam is scanned over the material of the sample 11. In addition, the sample 11 may be moved with the aid of a movable sample table (not illustrated) on which the sample 11 is situated. The first opening 25 may be adjacent to a first side 27 of the part 26 of the sample 11 to be analyzed and may have a first opening dimension O1 in a first direction, a second opening dimension O2 in a second direction, and a third opening dimension O3 in a third direction (see FIG. 4). The direction vectors belonging to the individual directions may be perpendicular to each other. The first side 27 of the part 26 of the sample 11 to be analyzed may be offset with respect to the particularly relevant location identified in the method step S4 by the desired thickness of the part 26 of the sample 11 to be analyzed.

Figure 5:
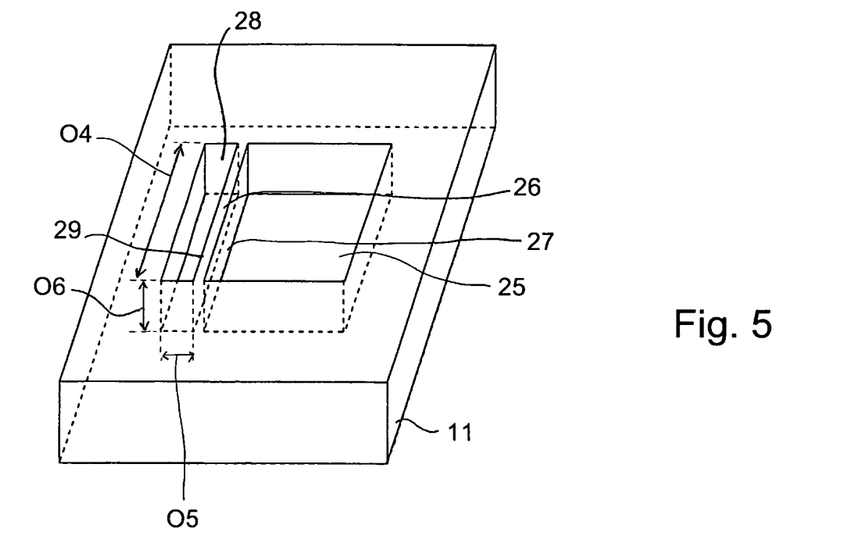
FIG. 5 shows another schematic representation of the sample of FIG. 3, the sample having two openings.

In a subsequent method step S7, a second opening 28 may be introduced in the material of the sample 11 with the aid of the ion beam (see also FIG. 5). The second opening 28 may be adjacent to a second side 29 of the part 26 of the sample 11 to be analyzed, which lies opposite to the first side 27 of the part 26 of the sample 11 to be analyzed. The second side 29 of the part 26 of the sample 11 to be analyzed may be situated close by and may contain the particularly relevant location identified in the method step S4.

The second opening 28 may have an opening dimension O4 in the first direction, an opening dimension O5 in the second direction, and an opening dimension O6 in the third direction. The opening dimension O5 of the second opening 28 may be considerably smaller than the second opening dimension O2 of the first opening 25. In contrast, the opening dimension O6 of the second opening 28 may be somewhat larger than the opening dimension O3 of the first opening 25. In another (not illustrated) embodiment, the first opening 25 and the second opening 28 may have substantially identical dimensions.

Figure 6:
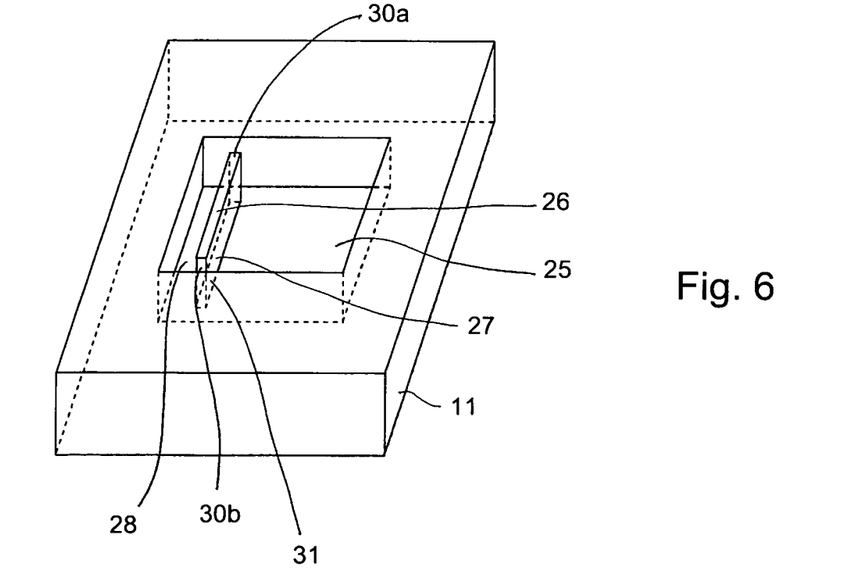
FIG. 6 shows another schematic representation of the sample of FIG. 3, a part of the sample to be analyzed being prepared for separating from the sample.

In a further method step S8, the second side 29 may be prepared by polishing with the aid of the ion beam. Subsequently, the sample 11 may be brought into a third sample position C (method step S9) in which, in the embodiment illustrated in FIG. 2, the sample 11 may be inclined to the vertical by approximately 10° to 20° (see FIG. 1). In a further method step S10, a lower surface 31 of the part 26 of the sample 11 to be analyzed may be separated from the sample material (see FIG. 6). For this purpose, the ion beam may be directed from the direction of the first opening 25 to the part 26 to be analyzed, and the part 26 of the sample 11 to be analyzed may be separated.

Subsequently, the sample 11 may be brought into the first sample position A again (method step S11). In this first sample position A, the part 26 of the sample 11 to be analyzed may now be separated, at its side surfaces 30a,b, from the sample material of the sample 11 (see FIG. 6). For this purpose, the ion beam may again be used (method step S12).

Figure 7:
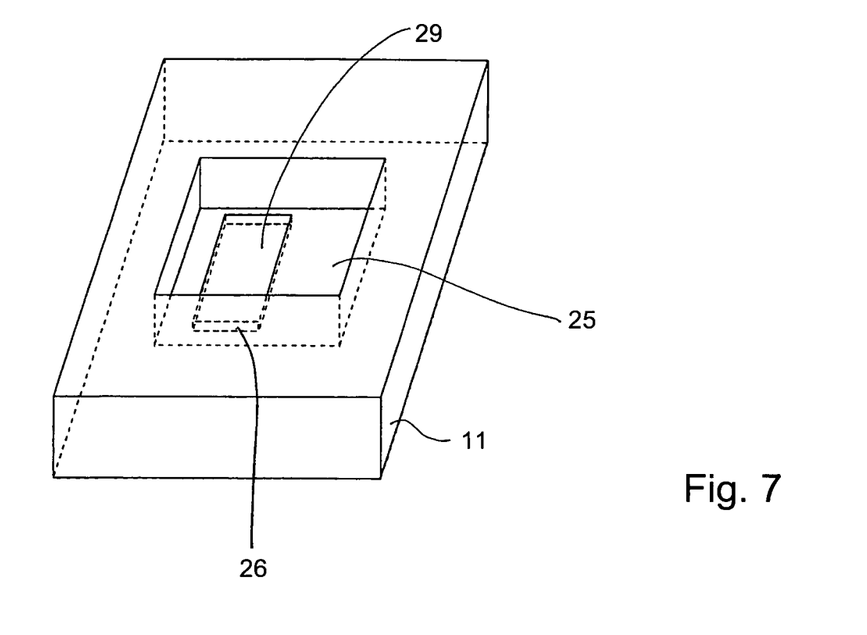
FIG. 7 shows another schematic representation of the sample of FIG. 3, the part of the sample to be analyzed being situated in the opening.

The part 26 of the sample 11 to be analyzed may drop into the first opening 25 by gravity (method step S13). Alternatively, the part 26 of the sample 11 to be analyzed may also be pushed into the first opening 25 with the aid of a manipulator device. In both alternatives, the part 26 of the sample 11 to be analyzed may be placed in such a way that the second side 29 is not covered and may be examined using a particle beam. The second side 29 of the part 26 of the sample 11 to be analyzed may be in the first opening 25 and may be inclined by approximately 90° with respect to the original orientation of the second side 29 of the part 26 of the sample 11 to be analyzed. A surface of the part 26 of the sample 11 to be analyzed, which corresponds to a cross-section surface through the sample 11, may thus be parallel to the sample surface and may thus be analyzed with the help of a particle beam incident perpendicularly or at least approximately perpendicularly on this cross-section surface (see FIG. 7). It is advantageous that the second side 29 of the part 26 of the sample 11 to be analyzed is exposed relatively late. The risk of the second side 29 being contaminated is thus reduced.

The part 26 to be analyzed, generated using the above-mentioned method, may have a dimensioning as mentioned previously. The part 26 of the sample 11 to be analyzed generated in this embodiment may have the form of a lamella. The above-mentioned dimensions of the part 26 of the sample 11 to be analyzed may be sufficiently large so it may be easily generated with the aid of the ion beam. Furthermore, they may be dimensioned in such a way that the part 26 to be analyzed may be accommodated in the first opening 25. In addition, no interaction particles are transmitted through the part 26 of the sample 11 to be analyzed. Instead, another examination method may be used, as discussed below.

To examine the second side 29, the sample 11 may be brought into the second sample position B, in which the electron beam may hit the second side 29 of the part 26 of the sample 11 to be analyzed perpendicularly (method steps S14 and S15). Secondary electrons and backscattered electrons are generated due to the interaction of the sample material with the electron beam and may be detected. The signals obtained via the detection may be analyzed and evaluated in a subsequent method step S16, in particular for imaging.

As an embodiment of the method according to the system described herein shows, the electron beam may be directed onto the part 26 of the sample 11 to be analyzed perpendicularly or approximately perpendicularly. The part 26 of the sample 11 to be analyzed may thus not be situated at an oblique angle to the incident electron beam. In this way, high spatial resolution is achieved. Furthermore, image distortions, which have been described above, are prevented.

In another embodiment of the method, it is additionally provided that the part 26 of the sample 11 to be analyzed may be examined with the aid of secondary ion mass spectrometry (SIMS). For this purpose, another method step may be introduced after the method step S16. In this other method step, the sample 11 may be brought into the first sample position A again. When the ion beam hits the surface of the part 26 of the sample 11 to be analyzed, secondary ions are generated, which may be examined using mass spectrometry. An ion mass analyzer 12, which generates a mass spectrum, may be provided for this purpose. The generated mass spectrum is then compared with a plurality of mass spectra which may be stored in a memory unit 14 of a control unit 13. The generated mass spectrum may be compared with the stored mass spectra with the aid of a processor 15 of the control unit 13. In this way it is possible to determine the material of which the sample 11 is composed.

Figure 8A:
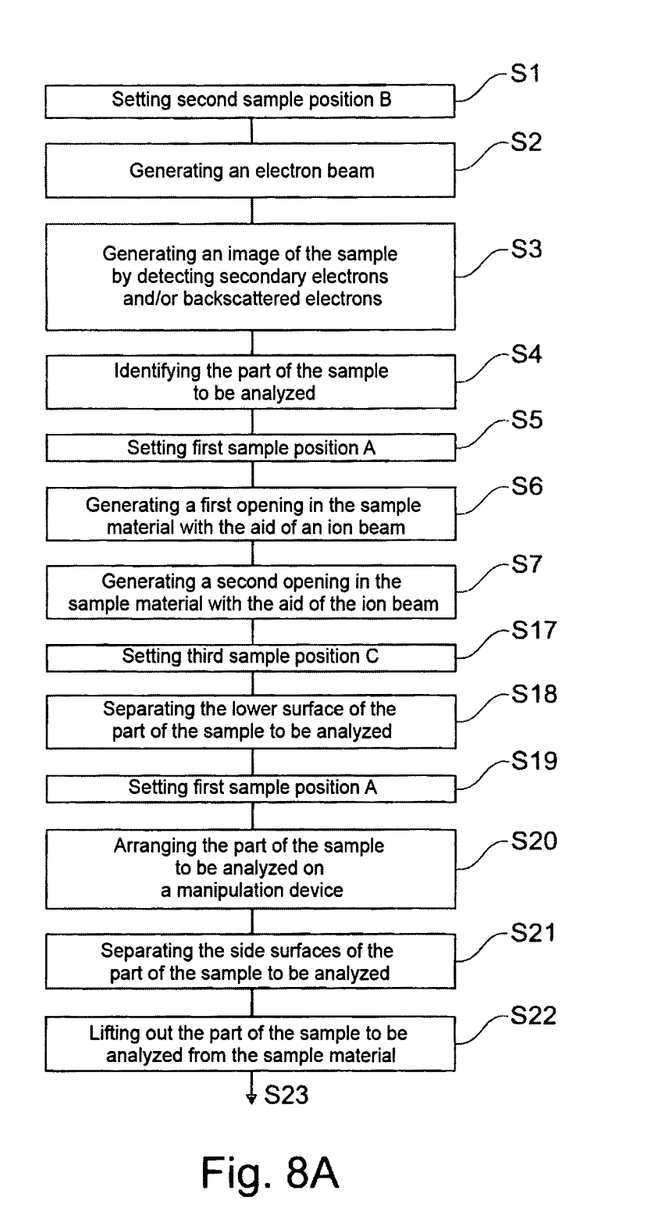
FIG. 8A, B show a schematic representation of another method for analyzing a sample according to an embodiment of the system described herein.
Figure 8B:
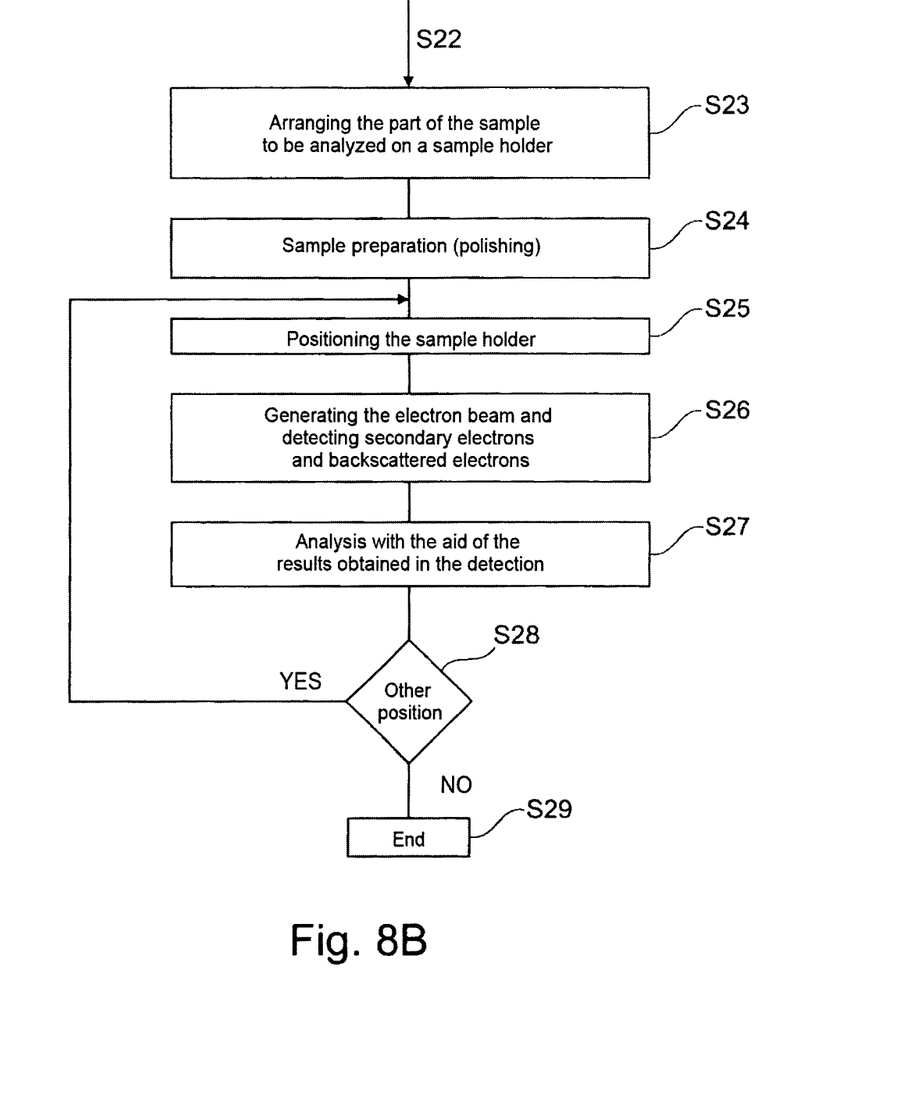

FIGS. 8A and 8B show another embodiment of the method according to the system described herein which may be carried out using the above-mentioned particle beam device 100. The embodiment now described is based on the method which is schematically illustrated in FIG. 2 and on the sample which is illustrated in FIGS. 3 through 7. Method steps S1 through S7 of FIGS. 8A and 8B correspond to method steps S1 through S7 of the method according to FIG. 2, so that reference is made to the above explanations regarding these method steps.

Unlike in the method according to FIG. 2, the method step S7 is followed by the method step S17 in which the sample 11 is brought into the third sample position C. In a further method step S18, a lower surface 31 of the part 26 of the sample 11 to be analyzed may subsequently be separated from the sample material. For this purpose, the ion beam may be directed from the direction of the first opening 25 to the part 26 to be analyzed, and the part 26 of the sample 11 to be analyzed may be separated. The sample 11 may then be brought to the first sample position A (method step S19).

In a further method step S20, the part 26 of the sample 11 to be analyzed may be arranged on a manipulation device. The manipulation device may be, for example, a micromanipulator. The part 26 of the sample 11 to be analyzed may be arranged, for example, with the aid of gas deposition or with the aid of mechanical clamps. The side surfaces 30a,b of the part 26 of the sample 11 to be analyzed may then be separated from the sample material with the aid of the ion beam (method step S21), and the part 26 of the sample 11 to be analyzed may be lifted out of the sample material (method step S22).

The part 26 of the sample 11 to be analyzed may now be brought to a sample holder and arranged thereon (method step S23). The part 26 of the sample 11 to be analyzed may be arranged, for example, with the aid of gas deposition or with the aid of mechanical clamps. In a subsequent method step S24, the side 29 of the part 26 of the sample 11 to be analyzed, which is to be examined with the aid of the electron beam further in the process, may now be prepared by polishing.

The sample holder may be movable, so that it is able to position the part 26 of the sample 11 to be analyzed, which is now attached to the sample holder (method step S25). Positioning takes place in such a way that an electron beam generated in method step S26 hits the side 29 of the part 26 of the sample 11 to be analyzed perpendicularly or at least approximately perpendicularly. The generated secondary electrons and backscattered electrons may be detected. The signals obtained via the detection may be analyzed and evaluated in a subsequent method step S27, in particular for imaging. If necessary, the method steps S25 through S27 may be repeated. This is checked in method step S28.

Figure 9:
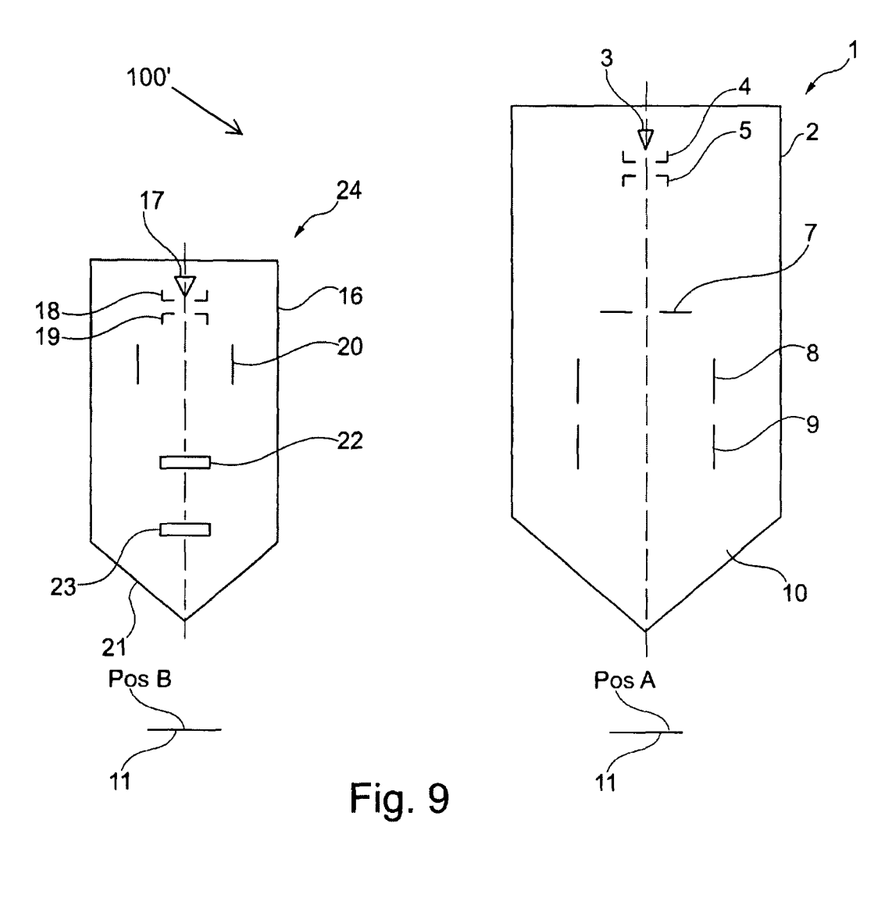
FIG. 9 shows a schematic representation of another particle beam device for analyzing a sample according to an embodiment of the system described herein.

FIG. 9 shows another embodiment of a particle beam device 100' using which the above-described method may be carried out. It basically differs from the embodiment of FIG. 1 only by the fact that the ion beam device 1 and the electron beam device 24 are situated parallel to one another and are positioned vertically.

The sample 11 is moved back and forth here between a first sample position A below the ion beam device 1 and a second sample position B below the electron beam device 24. To generate the part 26 of the sample 11 to be analyzed, the sample 11 may be placed in the first sample position A in such a way that it may be tilted.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for analyzing a sample, comprising:
providing a sample which is composed of at least one sample material;
identifying a part of the sample to be analyzed;
generating an opening in the sample material using a particle beam, wherein the opening is at least partially adjacent to the part of the sample to be analyzed;
separating, in order to completely detach, the part of the sample to be analyzed from the sample material using the particle beam, wherein, prior to the separating, the part of the sample to be analyzed is in a first orientation;
after separating the part of the sample to be analyzed, arranging the part of the sample to be analyzed within the opening, wherein the part of the sample to be analyzed is arranged within the opening in a second orientation different from the first orientation; and
analyzing the part of the sample to be analyzed while the part of the sample to be analyzed is within the opening, wherein the part of the sample to be analyzed is separated in such a way that the part of the sample to be analyzed has at least a first dimension in a first direction and a second dimension in a second direction, wherein the opening is generated in the sample material in such a way that the opening has a first opening dimension in the first direction and a second opening dimension in the second direction, wherein the first opening dimension is greater than or equal to the first dimension of the part of the sample to be analyzed, and wherein the second opening dimension is greater than the second dimension of the part of the sample to be analyzed.

2. The method as recited in claim 1, wherein the particle beam is a first particle beam and the method further comprising:
examining the part of the sample to be analyzed using a second particle beam.

3. The method as recited in claim 2, wherein, at least one of following:
an ion beam is used as the first particle beam, and
an electron beam is used as the second particle beam.

4. The method as recited in claim 2, wherein at least one of: backscattered electrons and electrons emitted from the sample are used to examine the part of the sample to be analyzed.

5. The method as recited in claim 2, wherein the part of the sample to be analyzed is identified using the second particle beam.

6. The method as recited in claim 1, wherein the part of the sample to be analyzed is separated from the sample material in such a way that the part of the sample to be analyzed drops by gravity into the opening generated in the sample material.

7. The method as recited in claim 1, wherein the part of the sample to be analyzed is separated using the particle beam directed to the sample from the direction of the opening.

8. The method as recited in claim 1, further comprising:
generating at least one section surface at the part of the sample to be analyzed by separating the part of the sample to be analyzed from the sample material, wherein the section surface is at least approximately perpendicular to a surface of the sample;

arranging the part of the sample to be analyzed in such a way that the section surface is parallel to the surface of the sample; and examining the section surface using the particle beam.

9. The method as recited in claim 1, further comprising:
generating at least one section surface by separating the part of the sample to be analyzed from the sample material, and
orienting the section surface with respect to the particle beam in such a way that the particle beam hits the section surface at least approximately perpendicularly.

10. The method as recited in claim 1, wherein the part of the sample to be analyzed is separated in such a way that the part of the sample to be analyzed has a third dimension in a third direction.

11. The method as recited in claim 10, wherein the part of the sample to be analyzed is separated in such a way that the second dimension in the second direction is in a range from 1 µm to 20 µm.

12. The method as recited in claim 11, wherein the second dimension in the second direction is in a range from 5 µm to 15 µm.

13. The method as recited in claim 10, wherein the opening is generated in the sample material in such a way that the opening has a third opening dimension in the third direction, and wherein the third opening dimension is greater than or equal to the third dimension of the part of the sample to be analyzed.

14. The method as recited in claim 1, wherein the opening is a first opening and is adjacent to a first side of the part of the sample to be analyzed, and wherein the separating of the part of the sample to be analyzed from the sample material includes generating a second opening in the sample material, the second opening being situated on a second side of the part of the sample to be analyzed which lies opposite to the first side of the part of the sample to be analyzed.

15. The method as recited in claim 1, wherein the part of the sample to be analyzed includes a surface, and wherein the surface, after being arranged in the opening, is oriented approximately 90° inclined with respect to an original orientation of the surface of the part of the sample to be analyzed before being arranged in the opening.

16. The method as recited in claim 1, wherein the part of the sample to be analyzed is separated using the particle beam directed to the sample through the opening.

17. A method for analyzing a sample, comprising:
providing a sample which is composed of at least one sample material;
identifying a part of the sample to be analyzed;
generating an opening in the sample material using a first particle beam in such a way that the opening is at least partially adjacent to the part of the sample to be analyzed;
separating, in order to completely detach, the part of the sample to be analyzed from the sample material using the first particle beam, wherein, prior to the separating, the part of the sample to be analyzed is in a first orientation;
after separating the part of the sample to be analyzed, arranging the part of the sample to be analyzed within the opening in the sample material, wherein the part of the sample to be analyzed is arranged within the opening in a second orientation different from the first orientation; and
examining the part of the sample to be analyzed using a second particle beam while the part of the sample to be analyzed is within the opening, wherein the part of the sample to be analyzed is separated in such a way that the part of the sample to be analyzed has at least a first dimension in a first direction and a second dimension in a second direction, wherein the opening is generated in the sample material in such a way that the opening has a first opening dimension in the first direction and a second opening dimension in the second direction, wherein the first opening dimension is greater than or equal to the first dimension of the part of the sample to be analyzed, and wherein the second opening dimension is greater than the second dimension of the part of the sample to be analyzed.

18. The method as recited in claim 17, wherein the part of the sample to be analyzed includes a surface, and wherein the surface, after being arranged in the opening, is oriented approximately 90° inclined with respect to an original orientation of the surface of the part of the sample to be analyzed before being arranged in the opening.

19. A device for analyzing a sample, comprising:
at least one first particle beam device operating in an identifying mode that uses a first particle beam to identify a part of the sample to be analyzed, wherein the sample is composed of at least one sample material;
at least one second particle beam device operating in an opening generation mode that generates an opening in the sample material using a second particle beam, the opening being at least partially adjacent to the part of the sample to be analyzed;
the at least one second particle beam device further operating in a separation mode that separates, in order to completely detach, the part of the sample to be analyzed from the sample material using the second particle beam, wherein, prior to the separating, the part of the sample to be analyzed is in a first orientation;
at least one manipulator that, after the part of the sample to be analyzed is separated, arranges the part of the sample to be analyzed within the opening, wherein the part of the sample to be analyzed is arranged within the opening in a second orientation different from the first orientation; and
the at least one first particle beam device further operating in an examining mode that examines the part of the sample to be analyzed using the first particle beam while the part of the sample to be analyzed is within the opening, wherein the part of the sample to be analyzed is separated in such a way that the part of the sample to be analyzed has at least a first dimension in a first direction and a second dimension in a second direction, wherein the opening is generated in the sample material in such a way that the opening has a first opening dimension in the first direction and a second opening dimension in the second direction, wherein the first opening dimension is greater than or equal to the first dimension of the part of the sample to be analyzed, and wherein the second opening dimension is greater than the second dimension of the part of the sample to be analyzed.

20. The device as recited in claim 19, wherein the first particle beam is an electron beam, and wherein the second particle beam is an ion beam.

21. A method for analyzing a sample having a sample surface, the method comprising:
identifying a part of the sample to be analyzed, including finding a particularly relevant location on the sample surface;
generating a first separating surface between the part of the sample to be analyzed and the sample at a distance from the particularly relevant location, the first separating surface being inclined with respect to the sample surface at an angle different from 0° and 180°;

generating a second separating surface between the part of the sample to be analyzed and the sample, the second separating surface being inclined with respect to the sample surface at an angle different from 0° and 180° and the second separating surface containing the particularly relevant location;

polishing only the second separating surface using a particle beam;

separating, in order to completely detach, the part of the sample to be analyzed from the sample by generating further separating surfaces;

orienting the second separating surface at least approximately perpendicular to the optical axis of a particle beam device; and analyzing the second separating surface by scanning the second separating surface using a focused particle beam and by detecting particles leaving the part to be analyzed on the side of the second separating surface, wherein at least the polishing step of the second separating surface and the step of analyzing the second separating surface are performed in the same vacuum chamber without the part to be analyzed being taken out of the vacuum chamber between the two steps, wherein the part of the sample to be analyzed is separated in such a way that the part of the sample to be analyzed has at least a first dimension in a first direction and a second dimension in a second direction, wherein the opening is generated in the sample material in such a way that the opening has a first opening dimension in the first direction and a second opening dimension in the second direction, wherein the first opening dimension is greater than or equal to the first dimension of the part of the sample to be analyzed, and wherein the second opening dimension is greater than the second dimension of the part of the sample to be analyzed.

22. The method as recited in claim 21, wherein at least one of: an electron beam and an ion beam is used as the focused particle beam, and wherein the focused particle beam provides a spatial resolution perpendicularly to a beam direction of the focused particle beam of less than approximately 5 nm.

23. The method as recited in claim 22, wherein the spatial resolution is less than approximately 1 nm.

\* \* \* \* \*